(12) United States Patent
Herregodts et al.

(10) Patent No.: US 12,408,999 B2
(45) Date of Patent: Sep. 9, 2025

(54) PATIENT SPECIFIC ROBOTIC BONE IMPLANT POSITIONING

(71) Applicant: UNIVERSITEIT GENT, Ghent (BE)

(72) Inventors: Stijn Herregodts, Geraardsbergen (BE); Jan Victor, Knokke-Heist (BE)

(73) Assignee: UNIVERSITEIT GENT, Ghent (BE)

( * ) Notice: Subject to any disclaimer, the term of this patent is extended or adjusted under 35 U.S.C. 154(b) by 894 days.

(21) Appl. No.: 17/606,300

(22) PCT Filed: Apr. 29, 2020

(86) PCT No.: PCT/EP2020/061834
§ 371 (c)(1),
(2) Date: Oct. 25, 2021

(87) PCT Pub. No.: WO2020/225045
PCT Pub. Date: Nov. 12, 2020

(65) Prior Publication Data
US 2022/0202511 A1 Jun. 30, 2022

(30) Foreign Application Priority Data
May 3, 2019 (EP) .................................... 19172536

(51) Int. Cl.
*A61B 34/30* (2016.01)
*A61B 17/15* (2006.01)
(Continued)

(52) U.S. Cl.
CPC ............ *A61B 34/30* (2016.02); *A61B 17/154* (2013.01); *A61B 17/8866* (2013.01); *A61B 2034/108* (2016.02)

(58) Field of Classification Search
CPC . A61B 34/30; A61B 2034/108; A61B 17/154; A61B 17/8866
See application file for complete search history.

(56) References Cited

U.S. PATENT DOCUMENTS

2014/0188129 A1 7/2014 Kang
2015/0094736 A1 4/2015 Lightcap et al.
(Continued)

FOREIGN PATENT DOCUMENTS

EP       3127514 A1    2/2017
WO    2010138715 A1   12/2010

OTHER PUBLICATIONS

International Search Report and Written Opinion from PCT Application No. PCT/EP2020/061834, Jul. 20, 2020.
(Continued)

*Primary Examiner* — Sameh R Boles
(74) *Attorney, Agent, or Firm* — Workman Nydegger

(57) ABSTRACT

A robotic system is provided for assisting during bone surgery, adapted to control the position of a limb. The robotic system includes a robotic arm connected to a fixation device for rigidly connecting the distal bone to the robotic arm and allowing movement in six degrees of freedom. Specifically, the fixation device provides at least two fixation points to the distal bone. The first fixation point can be rigidly connected to the distal bone near the joint and the second fixation point can be rigidly connected to a distal position of the distal bone. The rigid connection of the distal bone to the robotic arm allows the robotic system to impose controlled movement on the distal bone in six degrees of freedom.

19 Claims, 5 Drawing Sheets

(51) Int. Cl.
*A61B 17/88* (2006.01)
*A61B 34/10* (2016.01)

(56) References Cited

U.S. PATENT DOCUMENTS

2015/0106024 A1    4/2015   Malackowski et al.
2017/0360512 A1*  12/2017   Couture ................ A61B 34/30
2018/0185100 A1*   7/2018   Weinstein ............. A61F 2/461
2021/0353311 A1*  11/2021   Lavallee ............... A61B 34/20

OTHER PUBLICATIONS

Extended Search Report from corresponding EP Application No. EP19172536.5, Sep. 24, 2019.

* cited by examiner

PATIENT SPECIFIC ROBOTIC BONE
PATIENT SPECIFIC ROBOTIC BONE IMPLANT POSITIONING

FIELD OF THE INVENTION

The invention relates to the field of bone replacement surgery. More specifically it relates to a fixation system including a robotic arm for improving positioning of a bone during bone implant surgery, for example during total knee arthroplasty (TKA).

BACKGROUND OF THE INVENTION

Several health conditions affect the bone (especially limb joints), for example wear of the contact surfaces of the bones. Occasionally, the health condition becomes severe, reducing the quality of life of a person significantly or even result in complete immobility of the joint. Symptoms of these conditions include reduced mobility of joint, chronic pain, etc., and surgery may become necessary to solve or attenuate such conditions.

However, keeping the limb or its bone in a defined position during surgery, or changing such positioning, is difficult, but it is very important in order to cut them in a proper way or for mobility testing; for example, during knee replacement surgery, or to reduce potential damage on the ligaments.

During surgery, bone cutting is usually performed manually. This operation depends on the human factor and the skill of the surgeon, it is a tiresome practice, and it may result in damage to nearby tissue or uneven cutting. Uneven cutting translates in suboptimal fitting of implants, longer recovery and possible complications such as wear, pain, etc. In order to relieve these problems, automatization of the cutting can be provided. However, this requires the machine (e.g. a robotic arm) to have accurate information regarding position and surface of the bone, as well as input regarding the cutting path. At least part of this information can usually be provided by scanning (such as CT scan) the bone. However, the reference position of the bone during the surgery itself is required.

Clamping the limb is a feasible possibility of easy and safe implementation, but the cushioning of the flesh and muscles makes an accurate positioning for the robotic arm difficult. Even worse, the muscles and fat and other soft tissue usually does not allow proper immobilization of the bone itself, which can produce damages or uneven cutting if the bone moves during surgery.

It is possible to set marks on the bone to provide a reference system to sensors. However, setting the plurality of marks take time and may introduce extra stress and damage in the already exposed bone.

In general, bone surgery can be optimized or at least improved. For example, a usual intervention is knee arthroplasty. More than 2 million interventions are performed on yearly basis and estimations predict an increase of this number to 3.5 million by 2030. However, current patient satisfaction falls around 75%, which illustrates the room for improvement. Both the high number of procedures and the limited satisfaction rate show the need of new technologies aimed at solve the problems of current interventions.

SUMMARY OF THE INVENTION

It is an object of embodiments of the present invention to provide bone fixation devices which give a stable fixation and allow controlled manipulation of at least one bone on a limb, for example a tibia, or a tibia and femur, during surgery (e.g. knee arthroplasty).

It is a further object to provide a system of bone positioning for providing good placement of implants during surgery (e.g. knee arthroplasty) to provide a high restoration of the functionality of the articulation, with minimal risk for post-operative stiffness or instability of the articulation. In some embodiments, the system is further adapted for providing intra-operative and post-operative testing.

It is a further object to provide an automated robotic arm and setup for providing accurate bone cutting with stable and controllable bone positioning and fixation. The present invention relates to a robotic system for assisting during bone surgery, the robotic system adapted to control the position of a limb including a distal bone, e.g. to control the position of a distal bone. The robotic system includes a robotic arm and a fixation device connectable to the robotic arm.

The fixation device is adapted for rigidly connecting the distal bone to the robotic arm. Such rigid connection is realized by a fixation device comprising at least two fixation elements which are connectable to at least 2 different locations along the length of the distal bone, for example to a proximal and distal region of the distal bone along the length of the distal bone, and the two fixation elements providing fixation to the distal bone in respectively a first and second set of degrees of freedom upon connection thereto. Fixating part A to part B in one degree of freedom or one direction may be defined as connecting part A to part B with the goal of limiting, for example disabling, movement of part A with respect to part B in that degree of freedom or that direction. Rigidly connecting part A to part B may be defined as connecting part A to part B in order to avoid movement, for example both translational and rotational movement, for example movement in 3 translation directions and 3 rotational directions, of part A with respect to part B. Preferably the first and the second fixation element together provide fixation to the distal bone in 6 DOF upon connection thereto. The fixation device assures that movements in the first and second set of degrees of freedom, e.g. in 6 DOF movements, exerted by the robotic arm or imposed by the robotic arm to the fixation device upon connection to the robotic arm, can be transferred to the bone, for example directly transferred to the bone.

The rigid connection between the robotic arm and the distal bone with the robotic system is adapted for imposing controlled movement on the distal bone in both the first and second set of degrees of freedom, i.e. in 6 degrees of freedom to the distal bone. As a result of the fixation device of the robotic system according to the present invention, the robotic arm is adapted to control movement of the distal bone in six degrees of freedom, e.g. to transfer its movements to the distal bone. In order to realize the rigid connection between the robotic arm and the distal bone, the fixation device according to the present invention comprises at least two fixation elements, i.e. a first and a second fixation element. The first fixation element is connectable to the proximal region of said distal bone for fixating the robotic arm with the distal bone at a first position, i.e. at a proximal region of the said distal bone, allowing the robotic arm to impose movement on the distal bone, in a first set of degrees of freedom. Fixating the robotic arm with the distal bone may comprise fixating the first fixation element with the distal bone such that, upon connection of the robotic arm to the fixation device, a fixation of the robotic arm with the distal bone is realized. Allowing the robotic arm to impose movement on the distal bone in a first set of degrees of freedom may be realized as follows. The first element is connectable to the proximal region of the distal bone and is provided for fixating the distal bone at a proximal region thereof in a first set of degrees of freedom. Upon connection of the robotic arm to the fixation device, the robotic arm is able to impose a controlled movement of the distal bone in these first set of degrees of freedom The second fixation element is connectable to a distal region of the distal bone, for fixating or rigidly connecting the robotic arm with the distal bone, to impose movement on the distal bone in a second set of degrees of freedom. Fixating the robotic arm with the distal bone may comprise fixating the second fixation element with the distal bone such that, upon connection of the robotic arm to the fixation device, a fixation of the robotic arm with the distal bone is realized. Allowing the robotic arm to impose movement on the distal bone in a second set of degrees of freedom may be realized as follows. The second element is connectable to the distal region of the distal bone and is provided for fixating the distal bone at a distal region thereof in a second set of degrees of freedom. Upon connection of the robotic arm to the fixation device, the robotic arm is able to impose a controlled movement of the distal bone in this second set of degrees of freedom The distal region of a bone, e.g. the distal region of a distal bone, may be defined as the region most distal from the torso conveying half of the length of the bone, e.g. the distal bone, or less, for example 30% of the length of the bone as measured from its extreme opposite to the torso.

It is an advantage of embodiments of the present invention that by providing proper fixation elements, actual control of movement of the distal bone can be obtained in six degrees of freedom.

It is an advantage of embodiments of the present invention that the position and rotation of the distal bone can be controlled in a stable way for example during surgery, in vivo, with a great freedom of movement by controlling the position and movement in six degrees of freedom, being provided in a simple way using two fixation elements, which additionally provides rigid attachment of the limb to the robotic arm.

It is an advantage of embodiments of the present invention that a fixation device comprising two fixation elements which are connectable to two different regions of the bone along the length of the bone, for example longitudinally distributed along the bone, for example a first fixation element connectable to a proximal region of the bone and second fixation element connectable to a distal region of the bone, can provide improved fixation of the bone to the fixation device. As a result of the improved fixation of the bone to the fixation device, the robotic system according to the present invention can also provide improved control of the movement of the bone by the robotic arm, when connecting the robotic arm to the fixation device and imposing a movement thereto.

Having two fixation elements separated by a distance along the bone, results in the advantageous possibility of tuning the robotic arm so small forces on the bone can still provide torque, thus protecting the bone structure.

It is an advantage of embodiments of the present invention that a fixation device comprising two fixation elements reduces stress on a bone, upon imposing a movement by the robotic arm on the fixation device, and thus upon imposing a movement to the bone. In particular, two fixation elements connectable to two different regions of the bone along the length of the bone, allow to distribute the forces and torques applied on the bone by the robotic arm over two fixation elements. In particular, two fixation elements connectable to two different regions of the bone along the length of the bone, reduce the risk of breaking the bone upon 6D controlled movement of the bone by the robotic arm, the robotic arm being rigidly connected to the bone.

In embodiments of the present invention the fixation device is adapted to fixate the bone, e.g. the distal bone, in six degrees of freedom. Thereto the first fixation element may be adapted for fixating the distal bone in a first set of the 6 degrees of freedom and the second fixation device may be adapted for fixating the distal bone in a second set of the 6 degrees of freedom, e.g. in the remaining of the six degrees of freedom. Providing a fixation device which is able to fixate a bone, e.g. a distal bone, in 6 degrees of freedom, has the advantage that the robotic system is able to provide improved control of the movement of the bone by the robotic arm in 6 DOF, when connecting the robotic arm to the fixation device, for example rigidly connecting the robotic arm to the fixation device, and imposing a movement in 6 DOF thereto. Connecting the first fixation element to a proximal region of said distal bone for fixating the proximal region of the distal bone in a first set of the 6 degrees of freedom allows the robotic arm, when connected to the fixation device, to control movement of the distal bone in the first set of 6 degrees of freedom when imposing a movement thereto. Connecting the second fixation element to a distal region of said distal bone for fixating the distal region of the distal bone in a second set of the 6 degrees of freedom allows the robotic arm, when connected to the fixation device, to control movement of the distal bone in the second set of 6 degrees of freedom when imposing a movement thereto.

In embodiments of the present invention the robotic system has the advantage that the position of the bone, when imposing a movement thereto, can be more accurately determined, reducing the need for additional position markers across the bone during a procedure or surgery.

In embodiments of the present invention the robotic system is adapted for simultaneously imposing a movement, preferably an identical movement, to both the first and second fixation element. Simultaneously imposing an identical movement to the 2 fixation elements, attached to different locations across the bone, e.g. a proximal and a distal region of the distal bone, results in improved control of the bone by the robotic system.

In embodiments of the present invention the first and the second fixation element of the fixation device are rigidly connected to each other, e.g. through a bar or other suitable connecting means. Such embodiment has the advantage that when connecting a robotic arm to the fixation device, e.g. to the rigid connection connecting the first and second fixation element, the robotic arm is able to simultaneously impose an identical movement to the 2 fixation elements, resulting in an improved control of the bone by the robotic system.

In embodiments of the present invention the robotic arm is adapted for simultaneously imposing an identical movement to both the first and second fixation element. This may be realized by a suitable rigid connection between the robotic arm and both the first and second fixation element. Alternatively, each fixation element may be attached to a separate robotic arm/system and an identical and simultaneous movement to both fixation elements may be imposed by providing a suitable control algorithm to both robotic arms/systems.

The first fixation element may provide fixation and control of movement of the distal bone in three orthogonal directions of translation and at least one axial rotation around the longitudinal axis of the bone in a plane perpendicular to said axis.

The second fixation element may provide support of the distal bone and control of movement of the distal bone (so the robotic arm can impose movement on the limb in additional degrees of freedom) over at least a further rotational degree of freedom, for example two degrees of freedom. It is an advantage of embodiments of the present invention that an additional support for movement on one or more further rotational degree of freedoms can be provided, for example the vargus/valgus rotation and/or the flexion/extension rotation, thus improving positioning and control of the distal bone. The robotic system may exert only torques and forces in the degrees of freedom that the fixation device is designed to fixate and control. The robotic system may comprise a mechanical device containing a number of actuators at least equal to the number of DOF necessary to be controlled in the proximal joint of the proximal bone, in combination with a mechanical linkage system that has the same result.

The distance between the first fixation element and the second fixation element may be at least 30% of the length of the distal bone, or at least 50% of said length.

It is an advantage of embodiments of the present invention that good control of the translations and rotations is provided, with limited or no risk of tilting or stress on the bone due to lever effect.

The robotic system may control the position of a limb including a proximal bone and the system further may comprise a further robotic arm or external mechanism and at least one further fixation device for a proximal bone connectable to the further robotic arm or mechanism, including at least one fixation element for the proximal bone for fixating the further robotic arm or frame with the limb, allowing the further robotic arm or frame to impose movement on the limb in at least one degree of rotational freedom. It may e.g. provide controlled movement in at least one degree of rotational freedom of the proximal bone. Optionally the system may further comprise a restrain for extra fixation of the joint with the torso (e.g. a belt or hip restrain or the like). It is an advantage of embodiments of the present invention that the proximal bone (e.g. femur) can be imposed motion and/or be fixed in a predetermined position, without any displacement or sliding from muscles or fat, allowing a good orientation for bone cutting during surgery.

One fixation element may include at least one or at least two pins for attaching to the distal bone in direct physical contact thereto. One fixation element may include at least one or at least two pins for attaching to the proximal bone in direct physical contact thereto.

The bone fixation device for restricting the movement of the proximal bone of a limb further may include a movable frame for adjusting the angle of the proximal bone with respect to the torso, the angle restricted to the predetermined plane. For example the mechanism can impose a movement in five degrees of freedom (two translational and three rotational degrees of freedom) or six degrees of freedom, where the bone is positioned by the mechanism and the joint with the torso (e.g. hip).

It is an advantage of embodiments of the present invention that the angle between the proximal bone and torso, as well as the angle between proximal and distal bone, can be chosen for different ligament testing, as well as for accommodating different tools, such as cutting tools during bone surgery.

The first fixation element may include at least two pins for attaching to the bone in direct physical contact thereto. It is an advantage that direct rigid attachment between the bone and the robotic arm can be provided, thus improving accuracy of actuation and positioning.

The robotic system may include a processing unit for controlling and fixing the position of at least the distal bone, the robotic system further may include a sensing system for measuring the position of at least the distal bone as part of said controlling and fixing. It is an advantage of embodiments of the present invention that the position and orientation of the distal bone, optionally of the proximal bone, can be programmed and accurately fixed in position for surgery, allowing a predetermined soft tissue stressed configuration if required.

The robotic system may further comprise beacons rigidly fixed to the bone fixation device for motion tracking of at least at the distal bone fixation device. It is an advantage of embodiments of the present invention that the position can be measured by sensors for good automatic control of the robotic arm.

The robotic system may include a data input of 3D model data of the bone based on imaging, at least the robotic arm adapted to impose movement on the limb to position the bone in accordance with the 3D model data. It is an advantage of embodiments of the present invention that the geometric characteristics (shape, size, etc.) of the bone can be taken into account to provide a proper positioning for surgery.

The limb may comprise a joint and corresponding ligaments and the system may be further adapted to perform ligament testing, the robotic arm adapted to provide motion to a distal bone of a limb with respect to the proximal bone of the limb, the robotic arm further including a sensor to measure the response of the ligaments of the joint between the distal bone and the proximal bone, for assisting in mechanical and/or kinematic alignment and/or soft tissue releases.

It is an advantage of embodiments of the present invention that ligament properties can be measured, which can be taken into account to plan surgery and/or positioning of implant. In some embodiments of the present invention, the system may provide suggestions for ligament release. In some embodiments, the robotic system can guide the surgeon to perform soft tissue releases by tensioning the soft tissue to be released. In some embodiments, the system is adapted to perform intra-operative measurements. For example, the force sensor between clamp and robot may measure the force exerted by the robot as a result of the applied movement. This force feedback can then be used to define the internal joint forces to enable laxity and stiffness testing of the joint. The results of those measurements can then be used in combination with the implant geometry and bone geometry to define or optimize implant position and predict post-operative knee laxity. The system may further include means for measuring the mass properties of the distal part of the limb. It is an advantage of embodiments of the present invention that the limb mass can be taken into account for the ligament testing.

Where in embodiments of the present invention reference is made to mass properties, reference may be made for example to the mass, or the center of mass, or any other parameter expressing mass related aspects of the bone (e.g. the distal bone).

The system may further be adapted to provide motion and simultaneous force measurement with the sensor, to determine the mass and center of mass of the distal bone in order to compensate for the effect of changed distal bone orientation on the force measurement, thus to avoid influence of the orientation of the distal bone on the derived internal knee force measurements.

The system further may be adapted to stabilize the limb for positioning an implant and/or cutting the bone. It is an advantage of embodiments of the present invention that the robotic arm may assist in positioning of a prosthesis, and also in cutting the bone, by fixing accurately and in a stable way the bone. For example, bone cutting may be performed by a surgeon or by the robotic system itself.

The system may further include a second robotic arm adapted to receive a cutting tool for cutting portions of the bone. It is an advantage of embodiments of the present invention that assisted or automatic cutting can be provided.

The robotic arm may be programmed to, after implants are installed, measure post-operative laxity. It is an advantage of embodiments of the present invention that after the implants are installed by the surgeon, the robotic arm can be used to perform an objective quality check of the intervention. It is a further advantage that final releases and adjustments can still be made, if necessary, at this stage of the surgery.

The further robotic arm may be configured to lock a cutting tool for cutting within a predetermined plane, the predetermined plane obtained from calculations and positioning data provided by the processing unit.

The further robotic arm may be configured to perform cutting supported by calculations and positioning data provided by the processing unit.

The system may further include a switch off mechanism for stopping the actuation of at least one robotic arm on at least the distal bone if the sensing system sense a motion beyond a predetermined safe threshold or a force beyond a safe threshold, for avoiding damages in the bone, ligaments and muscles.

It is an advantage of embodiments of the present invention that safety can be improved in a highly automatized surgical environment.

The present invention also relates to a software carrier including an algorithm for performing translational and angular movements on a distal bone in a robotic system for ligament testing, laxity testing, and for processing the measurements of the responses of the ligaments to the movements, and/or to calculate a cutting plane in accordance with the measurements, optional implant positioning, sensed positioning and input related to the type of implant, and/or to predict post-operative laxity.

It is an advantage of embodiments of the present invention that a robotic arm can be programmed to perform ligament measurement, which may assist in implant positioning and cutting planning, and it may be programmed also to assist in bone cutting.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
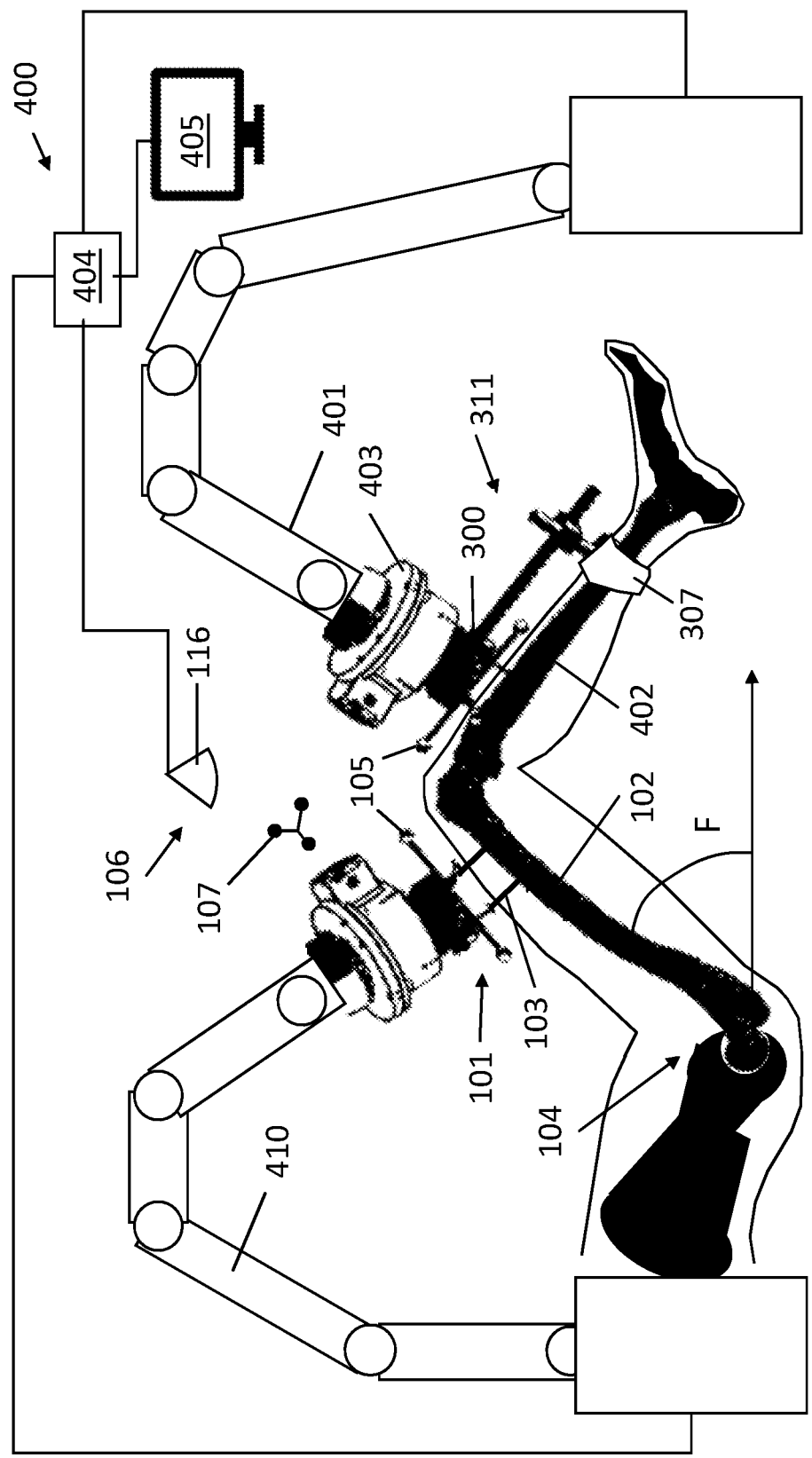
FIG. 1 illustrates a positioning system for a limb, including a pair of robotic arms comprising a fixation device for a femur and a tibia respectively, and the angle thereof with respect to the body, in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "fixation element", reference is made to holder or attachment means for holding, or attaching to, a bone, and which have strength enough to keep a bone in position and limit the movement of a bone in one or more directions. A fixation element may include anything which can be used to fix a bone of a limb, specifically on a region of a limb, for example which can be pinned or clasped to the bone, including pins, nails, rods, screws, clasps, pegs, bracers, etc.

The present invention provides devices and controllers, and in general a robotic system for assisting and/or for performing bone surgery. Embodiments of the present invention will be explained with reference to total knee arthroplasty (TKA). However, the present invention can be applied to other types of bone surgery, such as partial knee replacement, osteotomy, fracture reduction and the like. Further, the present invention can be also applied to other limbs, such as an arm or elbow.

Proximal Bone Fixation

In a first aspect, the present invention provides bone fixation devices including at least one fixation element, including e.g. two or more pins for attaching directly to the bone, thus providing good fixation of the bone. The contact between the bone and the fixation device can be done directly, not through layers of muscle and/or cartilage between the bone and the fixation device, but directly on the bone wall by nails or pins, or any other suitably stiff structure, e.g. a metal structure. Controllable positioning is possible via a robot arm holding the fixation element, rather than complete immobilization, allowing movement of the proximal bone. The fixation element can connect the proximal bone to the robot arm, or to a frame or the like, which allows the robotic arm to impose motion on the proximal bone in one or more degrees of freedom. The position of the femur can be imposed by the fixation element attached to the distal region of the proximal bone, which can be kept stable, by imposing movement in at least two (e.g. three) translations and one rotation degree of freedom. For example, the fixation element in the distal region of the proximal bone (e.g. the region of the shaft of the bone closer to the articulation with the other limb bone than to the torso, in case of a femur, close to the knee) allows the robotic arm to impose at least rotational motion. The strain is reduced thanks to the articulation with the torso (e.g. the hip). The robotic arm may provide, for example, extension and flexion of the proximal bone around the joint with the torso, the proximal bone being naturally connected thereto. Alternatively or additionally, it may provide valrus/valgus rotation, or even rotation around the bone axis (with reduced strain due to the stability provided by the articulation).

For the fixation element, a pin or nail is preferred to a clasp, because the orifice through the flesh and muscle to provide contact between bone and fixation element is smaller if the fixation element is a pin or nail than if it is a clasp, for which enough room should be provided by pushing all the muscles and tissue away. However, a clasp can be provided also, for example on a portion of a bone head not to be removed during surgery. The present invention is not limited to these fixation points or elements, and a non-invasive clasp around the skin of the limb can also be provided.

FIG. 1 shows a pair of robotic arms for the proximal and distal bones of a limb. In particular, it is shown the proximal bone fixation, with the specific fixation device 101 to fix a proximal bone, such as a femur 102, with only the flexion angle F with respect to the torso (e.g. with respect to the horizontal direction shown with an arrow from the joint 104 towards the foot) being variable. Thus, the angle F of the leg can be changed. For example, the hip flexion angle of a thigh may be controlled, for example by a robotic arm as shown in the figure, or by a mechanical frame or mechanism, for example by an external motor.

The fixation is provided outside the area of the joint surface which needs to be accessible for the surgery, because replacing of the pins, or of another fixation device, is not desired during surgery. The fixation may be provided by at least one pin nailed or drilled into the bone, for example a femur, or otherwise attached thereto, or at least two pins 103 as shown in FIG. 1, allowing the femur to rotate around the hip joint 104. It is noted that the fixation element includes pins which are directly attached to the bone by perforating locally the skin, muscles and other tissue of the leg. The pins may be distributed longitudinally. In some embodiments, the pins are distributed along the shaft of the bone. In the specific embodiment of FIG. 1, a device 101 with two pins 103 is shown attached to the bone (femur 102) along its length. However, the present invention is not limited to this configuration, and the two pins may be attached in different sides of the bone, for example at different sides at similar distance from the join, for example in diametral opposite sides. The distribution of the pins can be easily used also in combination with sensors, or beacons 105 for indicating the position to sensors, as it will be explained below with reference to the positioning system.

Figure 2:
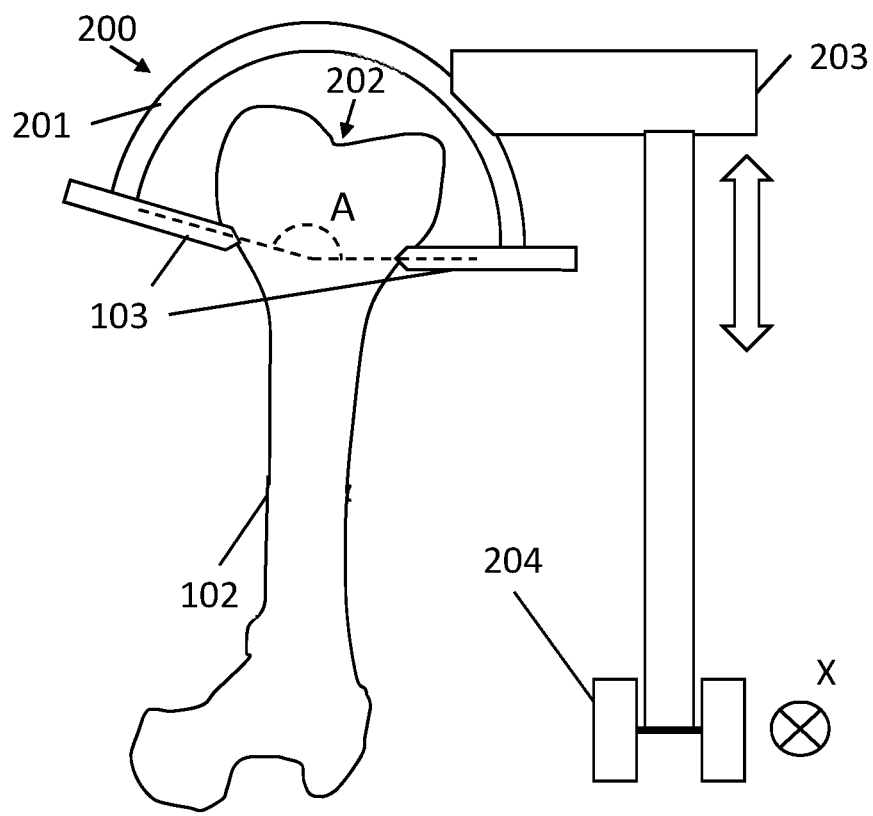
FIG. 2 illustrates another embodiment of a fixation device (a clamp) for a femur, in a frontal view, including a movable frame for adjusting the angle of the femur with respect to the body.

FIG. 2 shows a front view of the femur with an alternative bone fixation device, with the horizontal direction of FIG. 1 projected towards the viewer. In the specific example of FIG. 2, the bone fixation device includes a fixation element 200 including a clamp 201. The fixation is provided by at least two pins 103 which can be attached to different sides of the bone (e.g. femur 102) near the joint 202 to the distal part of the limb (e.g. near the knee), forming an angle A close to the 180°, thus being almost diametral opposite pins. Good attachment without a high strain can be obtained with the two pins attached to sides of the bone forming an angle between 90° and 120°.

The pins 103 may be include nails, or screws, or the like and these are used to hold the bones in vivo and to connect them to frames and/or robotic arms. Thus, the pins may be adapted for in vivo attachment. For example, they may be adapted to reduce or prevent infections, e.g. they may have antimicrobial properties.

The device in accordance with some embodiments of the first aspect of the present invention is movable to allow changing the position of the bone (its angle F with respect to the torso). For example, the fixation element (e.g. pins 103), and/or fixation device (e.g. clamp) 101, 201 may be anchored to an external frame or mechanism 203 for fixing the position of the bone (fixing its angle). The mechanism 203 may be movable and the position (flexing angle of the bone) may be selected by a user, e.g. a surgeon. The frame or mechanism 203 may include actuators, motors and the like to assist in the movement and select the angle with precision. For example, the frame may be adapted to tilt the fixation device 101 of FIG. 1, or it may be arranged to change the height and position, along the horizontal direction, of the clamp 201. The horizontal movement may be provided for example by rails. In any case, the bone is allowed to rotate around the joint with the torso (e.g. the femur can change the angle with respect to the hip joint).

The mass of the body and hip usually is enough for stabilization of the proximal end of the femur. Alternatively, the device may include a restrain, such as for example an extra fixation point close to the hip, for example a strap around the leg near the hip, for ensuring the femur does not slide due to accidental displacement, rotation or tilt of the hip bone, or in general to ensure that the femur has no translation component while selecting the angle.

Distal Bone Fixation

In a second aspect, the present invention provides distal bone fixation devices including at least two fixation elements longitudinally distributed along the distal bone. At least one fixation element may include, in some embodiments of the present invention, two or more pins or a clamp or clamping device for attaching directly to the bone, particularly close to the joint of the distal bone with the proximal bone, thus providing good fixation of the bone. The same advantages and features explained with reference to the first aspect can be applied with reference to the second aspect. The contact between the bone and the fixation device can be done directly, as in the device of embodiments of the first aspect. However, fixation is provided such that controllable positioning in space and bone orientation is possible, the device being adapted to be attached to a robotic arm. For example, the fixation device may include anchorage to a robotic arm. This allows proper, controlled positioning of the bones, allowing more freedom of movement, as the position of the bones (e.g. to separate the joint) does not need to be adjusted manually by medical staff, but it can be done automatically.

In particular, the first fixation element may be rigidly fixed to robot arm. For example, the robot arm connected to the distal bone by a first and second fixation element. The first fixation element is connectable to the proximal region of the limb (e.g. near the knee or elbow) and fixates the robotic arm to the limb, which may allow the robotic arm to impose movement on the limb, e.g. to fixate and control movement thereof, in a first set of degrees of freedom. The second fixation element is connectable to a distal region of the limb (e.g. near the foot or hand) for fixating the robotic arm with the limb, allowing imposing movement of the limb in a second set of degrees of freedom.

For example, the first fixation element is connectable to the proximal region of the distal bone and allows fixating the distal bone in at least three orthogonal translational directions and in at least one rotational direction. As a result of the first connection, when connecting, for example rigidly connecting, the robotic arm to the fixation device, the robotic arm allows imposing movement to the distal bone and controlling movement of the distal bone in at least three orthogonal translational directions and in at least one rotation direction, for example the axial rotation. The second fixation element may allow the robotic arm to impose movement on the limb in two further rotational directions in a safe way, without submitting the bone to strain or deformation. In particular, these rotational directions of movement may correspond to the valrus/valgus and extension/flexion rotational directions.

In total, the robotic arm can impose movement in 6 degrees of freedom to the fixation device and by the proper fixation of the bone by the fixation device, such movement is transferred and imposed to the distal bone The present invention is not limited to a first set of degrees of freedom being three translational orthogonal directions and one rotational direction, and a second set being two rotational directions. Depending on the fixation device, robot, etc. the different sets may include different degrees of freedom. For example, redundant degrees of freedom may be present in the sets.

Figure 3:
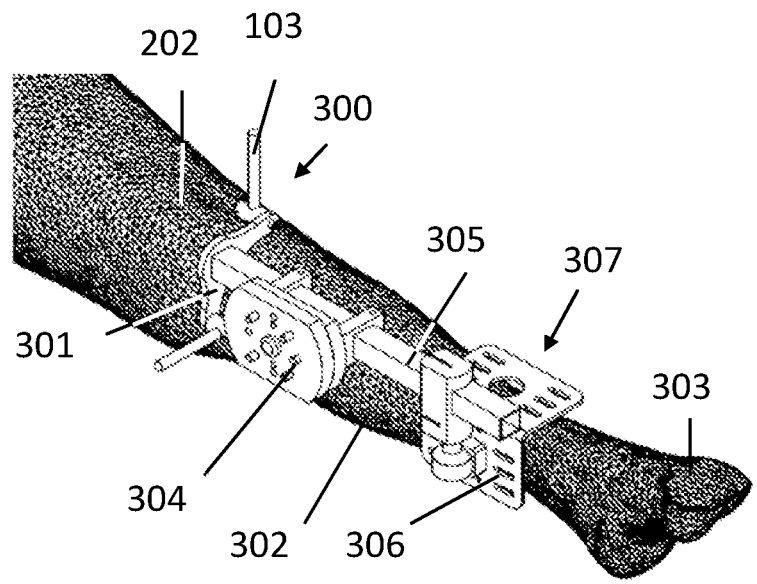
FIG. 3 illustrates an embodiment of a fixation system for a tibia, including a clamp similar to the one in FIG. 2, and further including a bracer for the angle and an anchorage for anchoring the device to a robotic arm.

FIG. 3 shows a specific fixation device 301, which may be a clamp, attached to a crus 302 (lower leg; in the context of the present invention, "crus" can be applied to the part of a leg, e.g. a human leg, between the knee and the foot) and extending from the region near the joint 202 towards the distal part of the crus 302, e.g. towards the foot 303. The device is adapted to fix the position of a crus bone, for example the tibia (inside of the crus and out of sight in FIG. 3). The first fixation element 300, close to the joint 202 between the distal bone and the proximal bone, includes two pins 103 directly attached to the bone. These pins are preferably not the standard surgical pins, which may not be resilient enough for some cases. Instead, the special shape may be directed to increase stability, for example a pin with a diameter larger than standard pins, where the diameter is reduced at the threaded part (to accommodate in a smaller hole on the bone), but a stiff shaft. The position of the tibia as well as its orientation can be selected and controlled (by for example an external robotic arm). In particular, the fixation element 300 (comprising the fixation device 301 and pins 103) of FIG. 3 can connect the tibia inside the crus 302 rigidly with a robotic arm, to which the device can be anchored through a plate with protrusions, screws, snaps or the like, or in general an anchorage 304 for a robotic arm. The fixation device 301 can be adjustable to the patient dimensions, for example it may include an extensible bar 305 for selecting the distance between fixation elements (e.g. pins or the like). The pins 103 which may hold the bone on the proximal part of the tibia, e.g. the first half, for example close to the knee joint 202, such as at the neck of the tibia or at the height of the tibial tuberosity or the soleal line. Similar fixation element 307 may be included in the distal portion of bone, for example below the medial border, e.g. close to the foot 303. Some of the pins may be distributed along the length of the bone, so as not to disturb the zone near the articulation where the main surgery takes place. In the distal portion of the bone, instead of pins, the fixation element 307 may include a non-invasive external clamp or bracer 306 as shown in the device of FIG. 3, in particular if the amount of fat or muscle in that region is low and good contact between the clamp and the bone through the skin of the crus 302 can be provided.

The present invention is not limited to lower limbs, and the fixation device may be adapted to hold a forearm, for example by attaching of pins to the ulna, adapting what is needed. For example in these cases, the positioning of the fixation elements can be adapted to corresponding areas in the ulna.

In order to perform accurate surgery and implant positioning, good fixation can be established, which allows providing a regular, even cutting. Additionally, a measurable positioning of the bone can be established, as well as accurate determination of the bone structure. As mentioned earlier, sensing elements 105 (e.g. beacons for position sensors, motion capture or motion tracking sensors) for detecting position may be included in the fixation device, and/or in a frame holding the fixation device, e.g. the clamp. Additionally, in some embodiments, extra sensors or beacons can also be attached to the bone directly, with nails or pins. This allows to register the motion of the bones accurately.

Non-Invasive Fixation

In order to provide a fixed position of the bone, it is not always necessary or possible to provide pins in the holes of drilled bones. In some cases, it is possible to provide a tight clamp around the leg, which still allows a good control of the bone.

Figure 4:
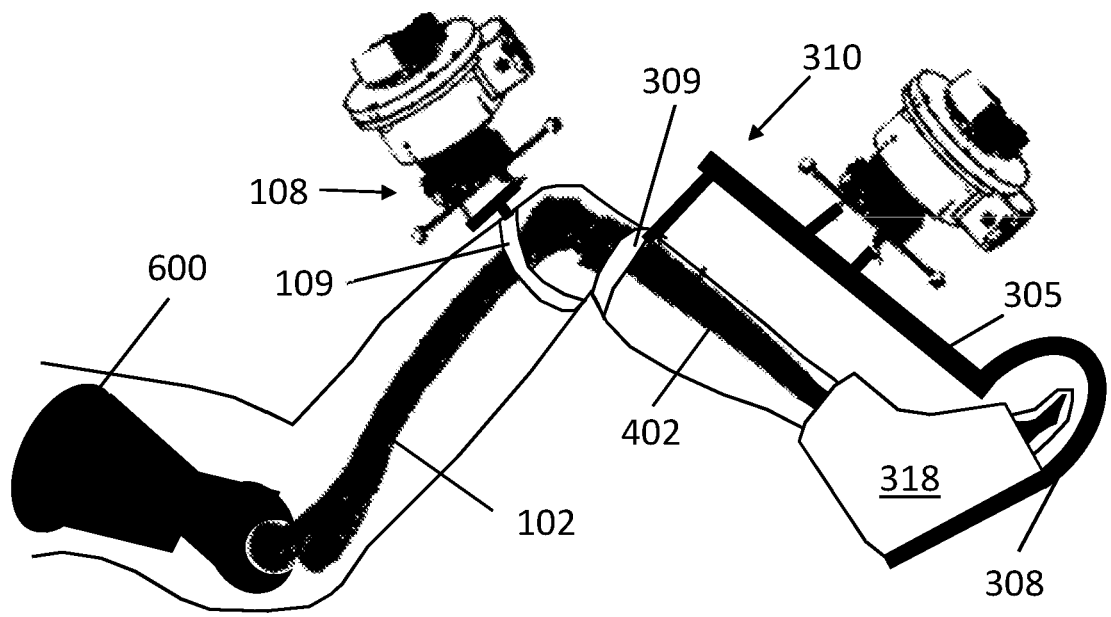
FIG. 4 illustrates an alternative non-invasive fixation system for a limb, including clamps and a foot holder.

FIG. 4 shows an exemplary embodiment where no perforating pins are used. The proximal bone 102 is being held by the weight of the body and hip 600 and by a fixation 108 including a clamp 109 e.g. a strap, or ring, positioned preferably so good grasp is provided, so the clamping is not done through thick layers of muscle, e.g. in an area between half of the proximal bone and the joint (e.g. near the neck of the femur, for example).

The distal bone is held by two fixation elements 308, 309 as before, but none of them includes pins or perforating elements. The first fixation element 309 includes a clamp, which may be analogous to the clamp 109 of the femur, explained above. The second fixation element 308 may comprise a foot holder, optionally including for example a shoe, an anchorage for a cast, or any other piece 318 adjustable to a foot, etc.

The two fixation elements 308, 309 for the distal bone are rigidly connected to a robotic arm, preferably also to each other (e.g. physically connected, e.g. through a bar 305), forming a fixation device 310, so as to provide enough freedom of movement (torque motions) and reduce stress on the hanging bone. The rest of systems for positioning, surgery, testing, bone cutting, etc. are compatible with the embodiment shown in FIG. 4.

Positioning System

In a third aspect, the present invention provides a positioning system, including embodiments of the fixation devices of the present invention.

The positioning system includes movable devices to select the position of the bones of a limb. For example, a movable frame or mechanism may be included, comprising mechanical elements such as slides, axles and the like for adjusting the angle of a proximal bone (e.g. femur) of a limb. For example, a robotic arm can be included, which allows six-dimensional movement of a distal bone (e.g. tibia) of a limb. Six-dimensional movement refers to translational movement in three non-colinear directions (e.g. linear movements in three perpendicular directions) and to angular movements with respect to three non colinear, for example perpendicular, axes (or, if preferred, angular movements in three intersecting planes).

Figure 5:
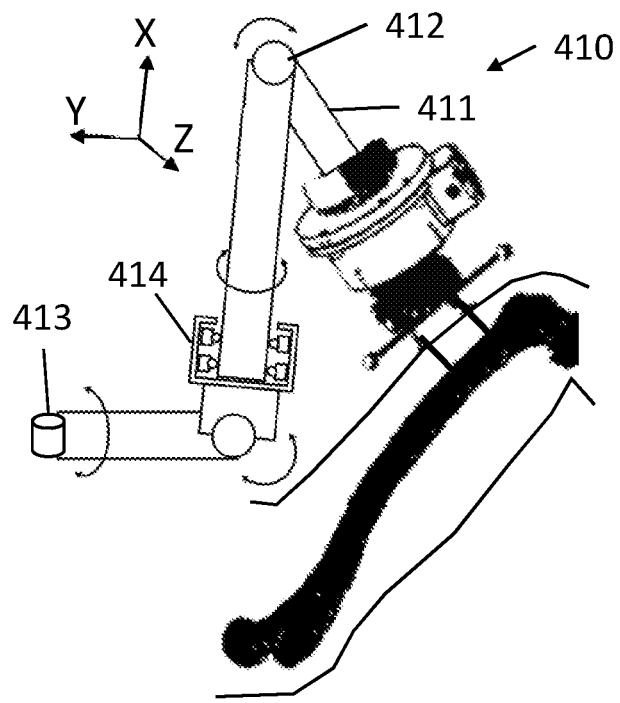
FIG. 5 illustrates an articulate robot arm and the degrees of freedom of motion of a limb bone based on the motions of the robot arm.

FIG. 5 shows a coordinate system and an exemplary positioning system including a robot arm 410 for holding a proximal bone, including a plurality of interconnected arms 411. The direction of the arm indicates the direction X. The positioning system may include levers 412 for rotation in the relative X-Y plane (rotation Z), hinges 413 for rotation in the relative X-Z plane (rotation Y), and axles 414, for allowing rotation on the Y-Z plane (rotation X). The arm may include redundant degrees of motion. A similar configuration can be used to position the distal bone.

The positioning system is adapted to select the position of at least the distal bone of the limb, which can be rigidly connected to a robotic arm 401 by two fixation elements. The positioning system may also be adapted to select the position of both the distal and the proximal bones.

Returning to FIG. 1, such positioning system 400, being a robotic system, is shown, including fixation device 101 for the femur (held by a robotic arm 410, optionally by a mechanism 203 as in FIG. 2), a fixation device 311 for a tibia and a robotic arm 401 which can impose motion and fix the position of a tibia 402 via the fixation device 311. The fixation device 311 includes a first fixation element 300 close to the joint 202 with the proximal bone 102, and a second fixation element 307 in the distal part of the distal bone, as also shown in FIG. 3. The robot 401 and the tibia 402 are rigidly connected by the fixation device 311. The first fixation element may provide a rigid connection to the robotic arm in a first set of degrees of freedom. As a result of the clamp connection, the bone can be moved in for example the direction of the three translations and the one rotation (e.g. three translational directions and the axial rotational direction).

The fixation of the second fixation element 307 may provide fixation of the robotic arm with the limb for imposing movement in a second set of degrees of freedom. For example, the second fixation element, together with the first fixation element 300, may improve control over further rotational movements (valrus/valgus rotation, extension rotation) of the tibia 402, and reduce strain on the bone than if only one fixation element 300 was used.

The distance between the first and second fixation elements 300, 307 may be at least 30% of the length of the distal bone, or at least 50% of said length, or even more. This improves stability and control, and reduces the chances of leveling the bone over a fixation element, which may result in uncontrolled ligament extension, stresses of the bone, or even damage.

The robotic arm 401 may include motors, actuators, rotors and the like to provide enough freedom of movement, with enough translational movement and angular movement, to the tibia 402, and it may include an interface for allowing control by a user, for example.

In the particular example of TKA, the surgery involves usually removing damaged bone, cartilage and other tissues.

Then, a femoral component should be fitted in the femur, a tibial component to the tibia and in some cases a patellar component. Computer-assisted TKA helps improving the alignment of the joint, which usually increases the duration of the prosthesis.

More in particular, orientation sensing and/or position sensing can be provided to the robotic arm using a sensing system 106, which may include sensing elements 105 such as the beacons for motion tracking, as shown in FIG. 1, but not limited thereto. For example, accelerometers, optical or magnetic sensors or the like may be provided on the bone, and/or directly on the fixation elements of the bone as part of the sensing system 106. If provided to the bone, they may be provided directly by pins. The sensing system 106 may have parts integrated in the robotic arm or external to the robotic arm, for example a sensor 116 may be included for tracking the motion of the limb, e.g. of the beacons 105 attached to the limb and/or to the fixation device. The external sensor 116 which provides position data to the robotic arm (in particular to the processing unit) may be a camera. The sensing system 106 may feed the position data directly to the robotic arm and/or its processing unit 404. The sensing system may also include a fixed position reference 107 for the sensor (e.g. camera).

In preferred embodiments, the fixation device 101, 301 (e.g. clamps) have beacons 105 mounted thereon. As a result of the rigid fixation of the clamps to the bone, the position of the bone can be calculated from the clamp position. This provides sensing without having to provide extra pin holes on the bone. An alternative setup provides beacons directly on the bone which can give the position of the bone with great accuracy.

In embodiments of the present invention, two limb fixation devices (e.g. leg fixation devices) can be provided, which allow to intra-operatively move the tibia with respect to the femur in a controlled way, and the possibility of combining them with a position control robot. This allows automatization of some aspects of the surgery, such as automatic and controllable accurate relative positioning of the limb, which improves handling of the limb during surgery.

For example, instead of the frame or mechanism 203 (e.g. a mechanical system comprising e.g. hinges and/or slides and/or motors) of FIG. 2 for selecting the position of the proximal limb, a further robotic arm can be included as shown in FIG. 1.

Positioning System and Ligament Testing

Today, a lot of methodologies exist and are used to position the implants during knee arthroplasty. Older techniques relate mainly to the bone geometry. In embodiments of further aspects of the present invention, bone geometry data can be combined with the patient specific ligament properties, which provides accurate information related for example balance assessment, to determine the proper position of the implants. Prior art setups allow very limited ligament property information and only very basic tests.

The bone fixation devices (e.g. clamps) of previous aspects may be part of the positioning system, for example an integral part of a positioning system including sensors and actuators for performing testing (e.g. ligament testing).

In some embodiments of the third aspect of the present invention, the robotic system allows performing characterization tests in the articulation, before, during and immediately after the surgery. For example, the characteristics of the ligaments can be studied and stored. This reduces complications during surgery, for example badly balanced knee after surgery due to improper placement of the implant, which may additionally cause continued pain, stiffness, instability, loosening or dislocation, or even infections. The robotic system allows, thanks to pre-operative, and/or intra-operative, and/or post-operative tests, to determine the proper position of the implants to restore the patient joint (e.g. knee) functioning as much as possible with minimal risk for post-operative stiffness or joint instability. For example, mechanical or kinematic alignment can be provided, e.g. can be programmed so the robotic arm can accurately determine the positioning and alignment.

For optimal outcome and fast revalidation, the 'natural feeling' of the knee joint should be retained as much as possible, if allowed by the pathological state of the knee. Ideally the feeling of the knee joint should be as close as possible to that knee in a healthy and functional state.

In embodiments of the present invention, the system allows minimizing proprioceptive changes as a result of the surgery, by minimizing the change in kinematics, and by restoring the post-operative stability of the knee joint. To obtain minimal proprioceptive disturbances, the post-operative knee functioning should mimic the native knee functioning as good as possible.

Therefore, the native knee characteristics can be determined by robotic testing, provided by the system of the present invention. Although the value and importance of pre-operative tests depend on the pathological state of the joint, the present invention also allows intra-operative and post-operative tests. Post-operatively, only remaining ligaments in combination with the implant geometry determine the passive knee functioning (stability/laxity). The system of the present invention also allows to determine the characteristics of those remaining ligaments intra-operatively, without the interaction of structures that are removed before implant installation.

The robotic arm 401 can provide for example translation of the limb in the space, for example in the three perpendicular directions of the space or combination thereof. Additionally, the robotic arm can provide angular movement, for example in three perpendicular planes of the space or combinations thereof, thus providing a six-degree-of-freedom (6DOF) robotic arm. Sensors 403 for force sensing (e.g. 6DOF force sensing) can be included in the robotic arm 401, for measuring the resistance or reaction of the limb to these movements (e.g. strain-stress measurements).

Figure 6:
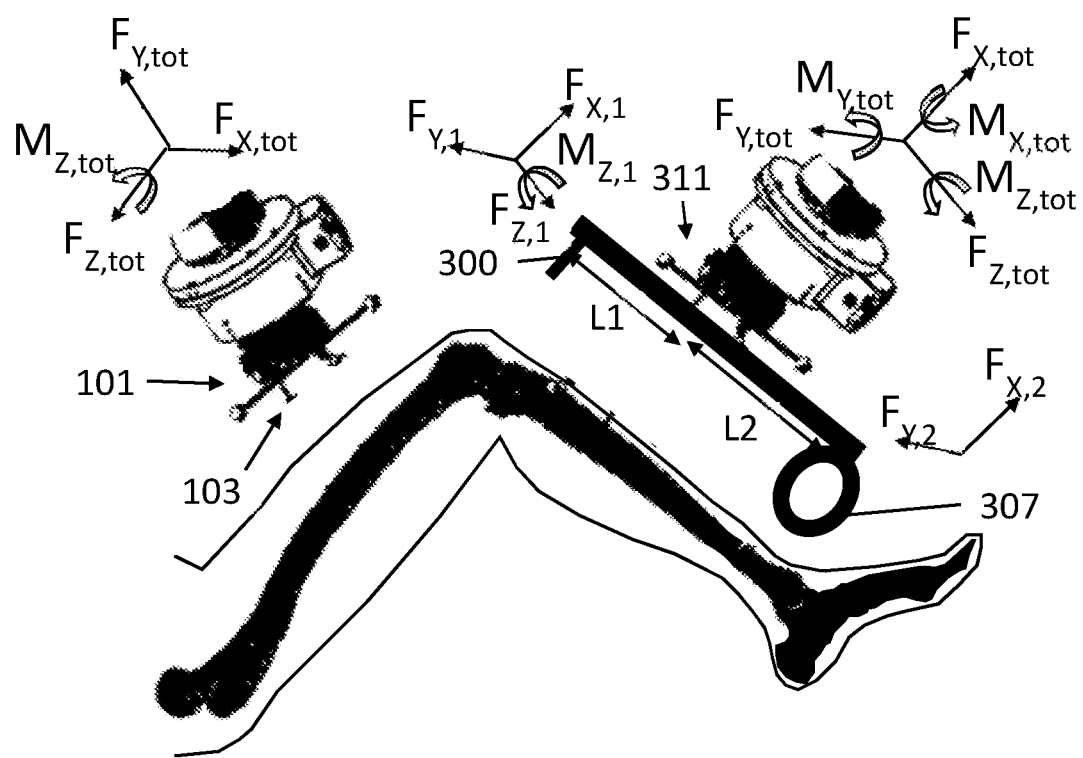
FIG. 6 illustrates the relationship between forces and torques on a leg, for the cases of a fixation device including a fixation element and a fixation device including two fixation elements.

FIG. 6 shows a force and momentum diagrams for a robot arm for a distal bone, with a fixation device 311 including a first fixation element 300 for fixating directly the bone position (by attaching nails directly on the bone) and another fixation element 307 for fixating the position of an ankle, with no bone perforation. The same is shown for a second arm for a proximal bone with a fixation device 101 comprising one fixation element 103. As shown in the force diagrams, the first fixation element 300 can exert forces in the bone in three orthogonal directions and torque in one rotational direction, but the second fixation element can only exert forces in two translational directions. The diagram shows how the majority of the forces are exerted by the clamp on the bone to illustrate the concept. In practice, small forces and torques can also be present in the other directions, but their magnitudes can be disregarded compared to the displayed forces and torques.

Considering Z the direction of the axis of the bone, X the perpendicular towards the robot arm, and Y the orthogonal to both, the total of the forces transmitted by the clamp to the robot arm 410 can be calculated as:

$$Fx,tot = Fx,1 + Fx,2$$

$Fy,tot=Fy,1+Fy,2$ $Fz,tot=Fz,1$

Torque is obtained from the forces and the the distances L1, L2 between the first and second fixation elements to the robotic arm which provides the motion.

$Mx,tot=L1·Fy,1-L2·Fy,2$ $My,tot=L2·Fx,2-L1·Fx,1$ $Mz,tot=Mz,1$

These give the forces and torques needed for the studies in the six degrees of freedom (6DoF), in three orthogonal translation directions and three orthogonal rotation directions. It is noted that the total forces and torques are calculated in a point on the centerline or axis of the bone.

Having two fixation elements separated by a distance (L1+L2) along the bone, results in the advantageous possibility of tuning the robotic arm so small forces on the bone can still provide torque, thus protecting the bone structure. As it can be seen in the fixation device 101 for the femur, which includes a fixation element 103, the system allows to exert force in three orthogonal directions while an additional rotational axial torque Mz can be exerted around the length direction of the femur. The axial torque may be provided with reduced strain on the bone, for example, by including two pins at different positions, e.g. slightly different distances from the extreme of the bone. It is preferred, for stability and reduced strain on the bone, that the fixing elements are placed in a distal region comprising 30% or less of the total length of the bone, measured from the distal extreme of the bone.

Force sensors and/or position sensors can be included (e.g. on the robotic arm, and/or on or integrated in the fixation device 311, etc.), for sensing the force on the limb upon movement of the robotic arm.

The response of the ligaments can be studied before and during the operation, as well as afterwards, via e.g. force and/or position sensors included e.g. in the fixation device. The fixture of the femur and of the tibia are thus important in order to obtain an accurate response of the ligaments, without influence of pressure or torsion of soft tissue (such as fat or muscle) other than of the ligaments. Positioning of the bones could also be provided to the 6DOF robotic arm with great accuracy of position and orientation of the bones. The position sensors introduced earlier, when applied to a 6DOF robotic arm, also serve to track the movement, and accurately perform the motions required for ligament testing. Motion tracking is a preferred option in this case, which may be used as position sensors or additionally to position sensors.

In embodiments of the present invention, the robotic arm 401 is adapted for obtaining the mass measurement of the distal part of the limb (e.g. the crus) being held by the robotic arm. For example, the force sensors 403 for sensing strain-stress can be used; however further sensors can be included in the arm for specifically sensing load. The measurement of the mass can be taken into account for the data processing of the response of the ligaments to the movements, for example as a correction factor, thus improving the accuracy of measurement.

For example, by performing iterative motions and with the use of the feedback of the force sensor, it is possible to put the knee in a position where the internal knee forces are minimized. In this position, a measurement can be performed to define mass properties, e.g. the mass and center of mass, of the distal bone.

This information can be used to correct the measured force during the tests, so only internal joint forces are measured and the effect of the gravity on the load sensor by changing the position of the distal limp is compensated. This can be done by calculation.

The present invention is not limited by these examples, and/or by other type of sensors could be used. For example, strain sensors, contact pressure sensors, position sensors, IMU sensor (accelerometer, gyroscope) and other sensor types can be used.

Testing at Different Stages of Surgery

After the bones have been fixed by the fixation devices of the first and second aspects of the present invention, but before incision on the knee has been performed, the characterization of the torsion and translation of the knee (6DOF force sensing) can be performed if the pathological state of the knee allows this. After the skin and flesh have been opened and the bones exposed, but before cutting the bone, the characterization can be repeated. A pre-measurement of mass properties (the mass and/or center of mass) can also be performed as explained earlier. For example, movement in the three directions can be performed, as well as movement following for example three rotations, for example including the valgus and varus angle, and/or the internal and/or external rotation of the knee ligaments, and/or the flexion angle of the tibia with respect of the femur. The responsive force to all these movements can be measured by the sensors 403 of the robotic arm 401 or by optional sensors in the clamping device.

In some embodiments of the present invention the fixation device of the proximal bone (e.g. the femur) may provide variation of the flexing angle of the bone, for example to optimize the position of the knee during the surgery, and/or to achieve sufficient range of motion of the knee joint while the position of the tibia is limited by the surgical table (the tibia cannot be positioned underneath and it should stay at a reasonable height with respect to the surgical table), and/or to position the tibia and femur in the optimal configuration for tibial mass estimation, for example.

The system may include software which allows processing the measurements performed by the robotic arm and combine them with inputs, for example with a kinematic model of the implants, and optionally with other data inputs such as the model of the patient's articulation, and/or bone surface (e.g. obtained by CT scan, echography or the like). The software may be included in a dedicated processing unit, or in the same processing unit 404 as the one that processes the signals from the sensing system 106. The processing unit 404 may include numerical optimization algorithms for processing the data and provide a model of positioning of the implant. The system may include an output 405, for example to a display unit or the like, for outputting the processed data and/or results based on the processed data, such as the results of the 6DOF force sensing, and/or implant positioning proposals and the like.

Hence, after characterization of the knee functioning (e.g. the native knee functioning and/or the knee with during operation, with remaining structures) by the robotic testing, the measurement data can be combined with a kinematic geometry-based model of the implants, and optionally with the patient's bone geometry, which could have been obtained previously by e.g. a CT scan, shape model or the like. Based on these inputs and on the numerical algorithms (with the possibility of self-learning, by holding knowledge of previous cases), the system can propose an implant position that the software may regard as optimal. The output 405 (display unit, such as a screen, etc.) may provide this information to medical staff, e.g. a surgeon. Additionally or alternatively, the software may propose potential ligament releases to obtain good and stable, e.g. healthy, post-operative knee characteristics (stability, laxity and kinematics) in the whole range of motion of the knee joint.

The passive knee properties after the operation, and even during and/or after recovery, can advantageously be predicted and even physically validated during the surgery by robotic testing before cuts are made, and/or before implants are inserted. To obtain a good, e.g. optimal consensus between alignment, knee stability and knee kinematics, the system (e.g. the robotic arm, the output of the processing unit 404 through the display or output 405) can guide the surgeon to perform releases before installing the implant, by stressing the ligament zones to be released.

It is noted that after the implant is performed, post operatively, the robotic arm may perform some measurements on the ligament (translational, angular movement of the distal bone of the limb), for obtaining a prognosis of the knee after replacement. The results may be processed in the processing unit 404 and they may be also compared with the native state of the knee and/or with the intra-operative measurements, to obtain an assessment of the outcome of the surgery. So, additionally to calculation of the implant positioning, it is possible to obtain predictive information regarding the post-operative passive knee stability based on the measurements (e.g. intra-operative tests) and processing algorithms of the results of measurements.

In summary, some embodiments of the third aspect provide an advanced robotic intra-operative test that can be used to determine patient specific ligament properties very precisely and accurately. The data obtained from the intra-operative testing and algorithms allow calculating implant position, based on patient specific ligament characteristics and implant geometry. Additionally, based on the ligament properties, in combination with the implant geometry, the post-operative knee stability can be predicted and approved by the surgeon before making any irreversible cuts. In current techniques, the cuts need to be made before representative ligament testing can be performed. The existing intra-operative tests only evaluate the knee in a very limited number of positions while the robotic system of the present invention is able to evaluate, predict and improve to ideally a healthy-like state the behavior for the complete real life operational range of the knee joint. Additionally, the present invention advantageously provides stable fixation and controlled manipulation of tibia and femur during knee arthroplasty. This may facilitate integration with automated robotic bone cutting techniques.

Surgery Setup

In a fourth aspect, the present invention provides a robotic system (e.g. including a holding robotic arm for holding bones) in accordance with embodiments of the previous aspect, and it further includes a cutting unit, thus providing a surgery setup.

Figure 7:
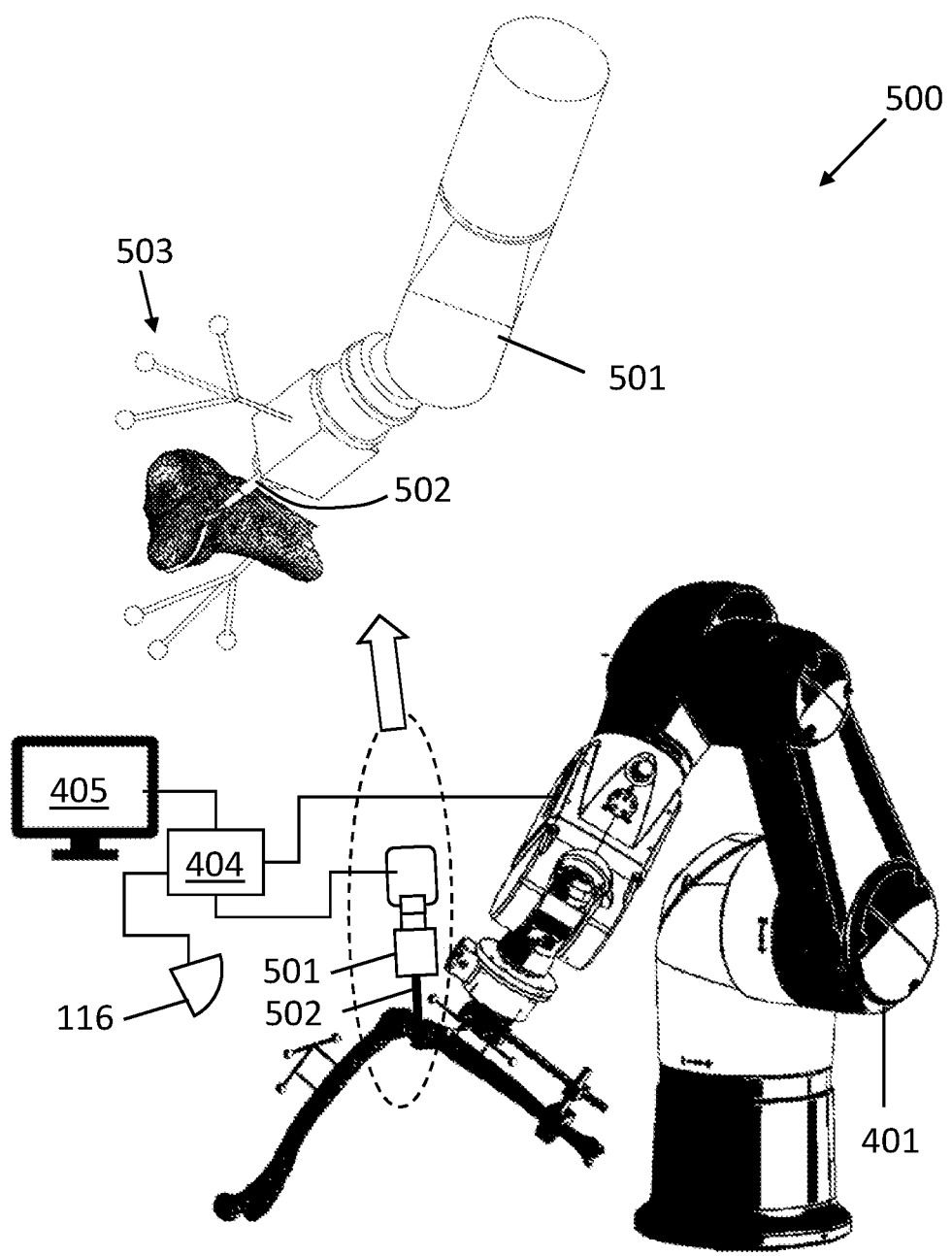
FIG. 7 illustrates an embodiment of a surgery setup including a positioning system and a cutting unit for cutting bone, as well as a zoom-in of the cutting unit.

FIG. 7 shows an exemplary robotic system 500 for assisting during surgery, in accordance with embodiments of the fourth aspect of the present invention, showing a cutting unit where the guide is a robotic arm 501 to which at least one cutting tool 502, e.g. bone cutting tool, can be attached and used to automatically perform bone cutting. It also includes controllers for automatic control and cutting, based on the sensed positioning of the limb. In embodiments of the present invention, the cutting unit is provided as an external robotic arm 501, distinct from the robotic arm 401 holding the bone. Additionally or alternatively, a cutting guide for a manually operated cutting tool can be included in the bone fixating device. In some embodiments, the cutting guide may be a computer assisted guide based of feedback from a camera system. The guiding device for the saw or cutting tool may be connected to the holding robot, the position thereof being adjustable in accordance with specific requirements of the procedure.

The robotic arm 501 including at least one cutting tool 502 may include a resection cutter, such as a saw, milling cutter or the like, and optionally clasps, wedges and other instruments for assisting cutting. The cutting unit may also include a sensing system 503, e.g. including sensing elements such as beacons, sensors, etc. This allows to define in every moment the position and orientation of the cutting tool 502. The processing unit 404 receives input from an interface, which may allow a surgeon to define the cutting path in either or both bones of the limb. The processing unit may receive data also from sensors, in particular at least from the positioning sensors (e.g. motion tracking system) installed on the limb, or preferably to the bone and/or on the fixation devices of the first and second aspects of the present invention. It may also receive data regarding the positioning of the robotic arm 401 and of the position and orientation of the cutting tool 502, e.g. from the sensing system of the robotic arm 501 for cutting bone. The processing unit 404 may be the same unit as the one that controls the movement of the holding robotic arm 401, but in other embodiments, a separate unit can be added, which is dedicated only to the cutting robotic arm (e.g. the processing unit for assisting a surgeon may be a dedicated processing unit, different for the unit for obtaining ligament characteristics).

In some embodiments, during a surgery, the processing unit 404 may determine an implant position and/or type/geometry, for example based on optimization algorithms, for which not only data input regarding the geometry of the bone, but also measurements performed on the ligament (by the robotic arm 401) can be taken into account. Also, ligament release may be suggested by the algorithm. Data related to positioning, ligament release, etc. can be displayed on a display or in general any output 405 or the like. After the proper implant position is determined, any ligament release is performed, and the surgeon approves the plan, a resection plan is calculated. A robotic arm 501 including a cutting tool 502 is integrated in the setup in accordance to embodiments of the fourth aspect of the present invention, which allows making the resections accurately according to the plan. The stable fixation of the femur and tibia creates good boundary conditions to allow automated cutting (next section).

As explained before, after the implants are installed by the surgeon, the robotic arm 401 holding the limb can be used to perform an objective quality check of the intervention by measuring the post-operative laxity accurately. This would be impossible with current technologies. The processing unit may analyze the post-operative measurements and it may be adapted to provide further information to the data output 405 (e.g. display). For example, final releases may be suggested, which can still be made if necessary at the late (e.g. final) stages of the surgery.

Assisted Bone Cutting

Some embodiments of the fourth aspect of the present invention provide a robotic arm 501 which limits the movement of the cutting tool 502 (for example, the movement of a milling cutter) to a plane. The plane may be determined or suggested by a processing unit 404, with algorithms for calculating the cutting plane in accordance with the information of the bone surface, the sensed position of the bone, the type and size of the implant, and even the ligament characteristics, with or without ligament release. If needed, ligament measurements can be repeated for better determining the cutting plane. The robotic arm 501 for cutting bone can lock the orientation of the cutting tool 502 within a predetermined plane. The predetermined plane can be obtained from calculations, positioning data, measurements, etc. provided by the processing unit 404. For example, within the predetermined plane, the tool 502 can turn, displace, change the angle following the surface of the bone, etc., but the tool does not tilt outside the plane. This ensures a regular, straight cutting which provides a flat, even surface on the bone. An implant attached to such surface will have good fitting and positioning, and it will result in faster recovery and longer lifetime. For example, no matter or fluids will accumulate in gaps, as it usually happens with gaps between an implant and an irregularity of the cut bone surface. In some embodiments, the cutting itself is performed by the surgeon, by moving the cutting tool 502 attached to the robotic arm 501 locked to the predetermined cutting path (e.g. cutting plane).

Some embodiments of the present invention may provide automatized cutting, for example automatic activation of the cutting tool, or even automatic displacement of the tool by the cutting unit (e.g. robotic arm 501), for example following a predetermined plane or, in general, a cutting path not limited to a single plane. The cutting may thus be supported by calculations and positioning data, e.g. provided by the processing unit 404. The good fixation of distal bone, and/or of proximal bone, provided by the positioning system 400 of previous aspects of the present invention also facilitates the resection in an automated way. Additionally the second robotic arm 501 can also utilize the sensing system 106 (e.g. including position sensors, beacons, etc. as already described), and/or may include also a sensing system 503, for example beacons or sensors to determine the position of the robotic arm 501 for cutting bone. For example, the same sensor 116 for tracking the position of the bones may be used to track the position of beacons on the second robotic arm 501. Alternatively, a second sensor (e.g. a second camera) or extra position sensors may be included for tracking the position of the cutting unit.

The cutting system and its software may be adapted to perform any or all the processes in one or more bones of a limb, for example it may perform cutting on a first and/or second bone of a joint, e.g. on a femur and/or on a tibia. Because the position is determined by sensing means (motion tracking, motion sensors, position sensors, etc.) in both bones, the surgery may have many or all of the steps with high level of automatization.

The cutting system may include further features to assist in the cutting, such as cutting force measurement and control (of pressure, speed, etc.). This may improve cutting by taking into account bone density, presence of soft tissue, reduction of temperature increase of the bone due to the cutting, etc. Further sensors, software or controllers and actuators (not shown in the picture) can be included in the robotic system 500. As mentioned earlier, a cutting guide can also be included, for example including camera feedback, for guiding a cutting tool, e.g. a manually operated cutting tool.

Also, thanks to the possibility of performing again ligament testing after the surgery, it is possible to make final adjustments on the ligaments, if necessary.

In embodiments of the third or fourth aspect of the present invention, the system or setup includes software for displaying selectable information to the surgeon through the output 405, which may be chosen or programmed, and which may be by default the most relevant parameters, taking into account each stage of the surgery.

Software and Algorithms

In a further aspect, at least one program is provided, for example software included in a processing unit 404 of the positioning system 400 or robotic system 500 for assisting during surgery. The software may include algorithms for providing, via the actuators of the robotic arm, motions (translational or angular movements, e.g. 6 dimensional motions) to the distal bone. It may include data treatment of inputs from position or motion sensors. It may also include algorithms for data treatment of input for image data such as surface studies of the bone, e.g. CT scans or the like. The software may include algorithms for obtaining and suggest (e.g. display) positioning of the implant. The algorithm may also take into account the mass of the distal part of the limb.

The program may include algorithms to calculate, based on the sensed positioning of the bone, and optionally on image data of the bone geometry, and optionally on ligament characteristics measurements, a cutting plan, e.g. a cutting path in a specific position or plane of the bone.

The cutting unit may also include software, or may be controlled by the software of the previous aspect of the present invention, for assisting in the cutting in the bone, e.g. for setting a cutting plane by blocking the movement of cutting tools to a plane according to the specific position and orientation of the bone, surface characteristics, etc. For example, the software may be programmed to perform automatic cutting of the bone or bones. The software may also include position data of the robot arm 501 of the cutting unit, for example obtained by sensors, by motion tracking (e.g. with a sensor 116), etc.

The present invention provided a highly automatized and independent surgical environment.

A safety system can be included, including a switch off mechanism for stopping the actuation of one or more robotic arms (e.g. the robot arm for positioning and/or for cutting), if the sensing system and/or sensors sense a motion beyond a predetermined safe threshold, or if a force threshold is exceeded, or if a torque threshold is exceeded, or a combination of these conditions. For example, if a combination of torsion and translation surpasses a predetermined threshold, which can be programmed taking into account the state of the ligaments, etc., the actuation of the robot stops and/or can be overridden by an operator. Thus, any chance of damages in the bone, ligaments and muscles are reduced or avoided, even in a highly automatized environment. This may be done by stopping the movement, returning to a previous state, e.g. by returning the followed path till a safe state is achieved, and/or by moving in the direction that reduces forces on the knee joint.

The invention claimed is:

1. A robotic system for assisting during bone surgery, the robotic system adapted to control a position of a limb including a distal bone, the robotic system including a robotic arm and a fixation device connectable to the robotic arm, the fixation device adapted for rigidly connecting the distal bone to the robotic arm, the fixation device comprising at least two fixation elements, wherein a first fixation element of the at least two fixation elements is provided at a first end of the fixation device and connectable to a proximal region of the distal bone for fixating the robotic arm with the distal bone allowing the robotic arm to impose movement on the distal bone in a first set of degrees of freedom and a second fixation element of the at least two fixation elements is provided at a second end of the fixation device opposite the first end and connectable to a distal region of the distal bone for fixating or rigidly connecting the distal bone to the robotic arm to impose movement on the distal bone in a second set of degrees of freedom, wherein a connection between the robotic arm and the fixation device is positioned between the first fixation element and the second fixation element, the robotic arm thus adapted for imposing movement in 6 degrees of freedom to the distal bone, wherein a distance between the first fixation element and the second fixation element is at least 30% of a length of the distal bone.

2. The robotic system of claim 1, the fixation device adapted for fixating the distal bone in the 6 degrees of freedom.

3. The robotic system of claim 1, the at least two fixation elements adapted for fixating the distal bone in the 6 degrees of freedom, the first fixation element adapted for fixating the distal bone in a first set of the 6 degrees of freedom and the second fixation element adapted for fixating the distal bone in a second set of the 6 degrees of freedom.

4. The robotic system of claim 1, the robotic system being adapted for simultaneously imposing an identical movement to both the first and second fixation element.

5. The robotic system of claim 1, the robotic arm being rigidly connectable or rigidly connected to both the first and the second fixation element.

6. The robotic system of claim 1, the first fixation element and the second fixation element being rigidly connectable or rigidly connected to each other.

7. The robotic system of claim 1, wherein the first fixation element is connectable to the proximal region of the distal bone for fixating the robotic arm with the distal bone allowing the robotic arm to impose movement on the distal bone in three orthogonal directions of translation and at least one axial rotation around a longitudinal axis of the distal bone in a plane perpendicular to said longitudinal axis.

8. The robotic system of claim 1, wherein the second fixation element is connectable to the distal region of the distal bone for fixating or rigidly connecting the distal bone to the robotic arm allowing the robotic arm to impose movement on the distal bone in at least a rotational degree of freedom being flexion-extension rotation and/or vargus-valgus rotation.

9. The robotic system of claim 1 adapted to control a position of a proximal bone of the limb, the system comprising a further robotic arm or an external mechanism and a fixation device connectable to the further robotic arm or the external mechanism, including at least one further fixation element connectable to a distal region of the proximal bone for fixating the further robotic arm or the external mechanism with the proximal bone of the limb allowing the further robotic arm or the external mechanism to impose movement on the proximal bone of the limb in at least one degree of rotational freedom.

10. The robotic system of claim 1 wherein the first fixation element includes at least two pins for attaching to the distal bone in direct physical contact thereto.

11. The robotic system of claim 1 further including a processing unit for controlling or fixing a position of at least the distal bone, the robotic system further including a sensing system for measuring the position of at least the distal bone as part of said controlling and fixing.

12. The robotic system of claim 1 further comprising beacons rigidly fixed to at least the distal bone fixation device for motion tracking of at least the distal bone fixation device.

13. The robotic system of claim 1, the limb comprising a joint and corresponding ligaments, the robotic system further being adapted to perform ligament testing, the robotic arm adapted to provide motion to a distal bone with respect to a proximal bone of the limb, the robotic arm further including a sensor to measure a response of ligaments of a joint between the distal bone and the proximal bone, for assisting in implant alignment and/or soft tissue releases.

14. The robotic system of claim 1 further including means for measuring mass properties of a distal part of the limb.

15. The robotic system of claim 14, the system being further adapted to provide motion and simultaneous force measurement with the means for measuring mass properties of the distal part of the limb, to determine a mass and center of mass of the distal bone in order to compensate for an effect of changed distal bone orientation on the force measurement, thus, to avoid influence of an orientation of the distal bone on derived internal knee force measurements.

16. The robotic system of claim 1 further adapted to stabilize the limb for positioning an implant and/or cutting the bone.

17. The robotic system of claim 1 further including a second robotic arm adapted to receive a cutting tool for cutting portions of the bone.

18. The robotic system of claim 1 wherein the robotic arm is programmed to, after implants are installed, measure post-operative laxity.

19. The robotic system of claim 1 wherein the first fixation element is connectable to the proximal region of the distal bone by directly attaching to the distal bone, and
    wherein the second fixation element is connectable to the distal region of the distal bone by non-invasively attaching to the distal bone.

\* \* \* \* \*